(12) United States Patent
Anderson et al.

(10) Patent No.: US 11,554,255 B2
(45) Date of Patent: Jan. 17, 2023

(54) MEDICAL DEVICE FOR SEPTAL CROSSING WITH TRAPPING FEATURES

(71) Applicant: BOSTON SCIENTIFIC SCIMED, INC., Maple Grove, MN (US)

(72) Inventors: James M. Anderson, Corcoran, MN (US); Jose A. Meregotte, Blaine, MN (US); Eric Michael Petersen, Maple Grove, MN (US); David John Onushko, Maple Grove, MN (US); Lloyd Radman, Blaine, MN (US); Joseph Edward Adriaens, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1043 days.

(21) Appl. No.: 16/245,893

(22) Filed: Jan. 11, 2019

(65) Prior Publication Data

US 2019/0217063 A1   Jul. 18, 2019

Related U.S. Application Data

(60) Provisional application No. 62/616,848, filed on Jan. 12, 2018.

(51) Int. Cl.
*A61M 25/09* (2006.01)
*A61B 17/00* (2006.01)
(Continued)

(52) U.S. Cl.
CPC ......... *A61M 25/09* (2013.01); *A61B 17/0057* (2013.01); *A61M 25/003* (2013.01);
(Continued)

(58) Field of Classification Search
CPC ............ A61M 25/0169; A61M 25/003; A61M 2025/09008; A61M 25/09; A61M 25/104;
(Continued)

(56) References Cited

U.S. PATENT DOCUMENTS 5,327,885 A    7/1994   Griffith
7,833,197 B2  11/2010   Boutilette et al.
(Continued)

FOREIGN PATENT DOCUMENTS

WO    9211055 A1    7/1992
WO    9411038 A1    5/1994
(Continued)

OTHER PUBLICATIONS

International Search Report and Written Opinion dated May 6, 2019 for International Application No. PCT/US2019/013258.

*Primary Examiner* — Christine H Matthews
*Assistant Examiner* — Joshua Daryl D Lannu
(74) *Attorney, Agent, or Firm* — Seager, Tufte & Wickhem LLP

(57) ABSTRACT

Medical devices and methods for making and using medical devices are disclosed. An example medical device may include an elongate shaft having a proximal end region and a distal end region. A first lumen may be defined in the shaft. A second lumen may be defined in the shaft. The distal end region may include a common lumen region in fluid communication with the first lumen and the second lumen. A deflectable member may be disposed within the shaft. The deflectable member may be designed to shift between a first configuration where the deflectable member directs a first medical device disposed within the common lumen region into the first lumen and a second configuration where the deflectable member allows a second medical device to move between the common lumen region and the second lumen.

18 Claims, 19 Drawing Sheets

(51) Int. Cl.
*A61M 25/00* (2006.01)
*A61M 25/10* (2013.01)
*A61B 17/12* (2006.01)
*A61M 25/01* (2006.01)
*A61M 29/00* (2006.01)

(52) U.S. Cl.
CPC .................. *A61B 17/12122* (2013.01); *A61B 2017/00243* (2013.01); *A61B 2017/00526* (2013.01); *A61B 2017/00592* (2013.01); *A61B 2017/00623* (2013.01); *A61B 2017/00867* (2013.01); *A61B 2017/1205* (2013.01); *A61M 25/0074* (2013.01); *A61M 25/0169* (2013.01); *A61M 25/104* (2013.01); *A61M 29/00* (2013.01); *A61M 2025/09008* (2013.01)

(58) Field of Classification Search
CPC .............. A61M 29/00; A61M 25/0074; A61B 2017/00623; A61B 2017/00526; A61B 2017/00867; A61B 17/0057; A61B 2017/1205; A61B 2017/00592; A61B 2017/00243; A61B 17/12122
See application file for complete search history.

(56) References Cited

U.S. PATENT DOCUMENTS

| | | | |
|---|---|---|---|
| 8,221,357 B2 | 7/2012 | Boutilette et al. | |
| 8,556,857 B2 | 10/2013 | Boutilette et al. | |
| 8,784,362 B2 | 7/2014 | Boutilette et al. | |
| 2009/0182200 A1* | 7/2009 | Golden | A61M 25/09 |
| | | | 600/153 |
| 2011/0077463 A1* | 3/2011 | Hirota | A61B 5/6852 |
| | | | 600/114 |
| 2014/0276611 A1* | 9/2014 | Banerjee | A61M 25/003 |
| | | | 604/510 |

FOREIGN PATENT DOCUMENTS

| | | | | |
|---|---|---|---|---|
| WO | WO-9411038 A1 * | 5/1994 | ............. | A61B 17/22 |
| WO | 9069499 A1 | 11/2000 | | |
| WO | 2007033052 A2 | 3/2007 | | |
| WO | 2018132782 A1 | 7/2018 | | |

\* cited by examiner

MEDICAL DEVICE FOR SEPTAL CROSSING WITH TRAPPING FEATURES

CROSS-REFERENCE TO RELATED APPLICATIONS

This application claims the benefit of priority under 35 U.S.C. § 119 of U.S. Provisional Application No. 62/616,848, filed Jan. 12, 2018, the entire disclosure of which is hereby incorporated by reference.

TECHNICAL FIELD

The present disclosure pertains to medical devices, and methods for manufacturing medical devices. More particularly, the present disclosure pertains to medical device for septal crossing with trapping features.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. A medical device is disclosed. The medical device comprises: an elongate shaft having a proximal end region and a distal end region; a first lumen defined in the shaft; a second lumen defined in the shaft; wherein the distal end region includes a common lumen region in fluid communication with the first lumen and the second lumen; and a deflectable member disposed within the shaft, the deflectable member being designed to shift between a first configuration where the deflectable member directs a first medical device disposed within the common lumen region into the first lumen and a second configuration where the deflectable member allows a second medical device to move between the common lumen region and the second lumen.

Alternatively or additionally to any of the embodiments above, the deflectable member includes a spring ribbon wire.

Alternatively or additionally to any of the embodiments above, the deflectable member includes a one-way valve.

Alternatively or additionally to any of the embodiments above, the first lumen, the second lumen, or both have a constant diameter.

Alternatively or additionally to any of the embodiments above, along at least a portion of the length of the shaft, the first lumen, the second lumen, or both have a variable diameter.

Alternatively or additionally to any of the embodiments above, the deflectable member is biased to be in the first configuration.

Alternatively or additionally to any of the embodiments above, further comprising a trapper balloon disposed within the first lumen.

Alternatively or additionally to any of the embodiments above, the shaft defines a third lumen in fluid communication with the trapper balloon.

Alternatively or additionally to any of the embodiments above, the shaft defines a fourth lumen and wherein a shapeable member is disposed within the fourth lumen.

Alternatively or additionally to any of the embodiments above, further comprising a distal balloon coupled to the distal end region of the shaft.

Alternatively or additionally to any of the embodiments above, the shaft defines a fifth lumen in fluid communication with the distal balloon.

Alternatively or additionally to any of the embodiments above, the distal balloon includes a compliant material.

A dilator is disclosed. The dilator comprises: an elongate shaft having a proximal end region and a distal end region; a guidewire lumen defined in the shaft; a needle lumen defined in the shaft; wherein the guidewire lumen and the needle lumen merge into a common lumen along the distal end region of the shaft; and a deflectable member disposed within the shaft, the deflectable member being designed to shift between a first configuration where the deflectable member is configured to direct a guidewire device from the common lumen into the guidewire lumen and a second configuration where the deflectable member is deflected in order to allows a needle device to move between the common lumen and the needle lumen.

Alternatively or additionally to any of the embodiments above, the deflectable member includes a spring ribbon wire.

Alternatively or additionally to any of the embodiments above, the deflectable member includes a one-way valve.

Alternatively or additionally to any of the embodiments above, the deflectable member is biased to be in the first configuration.

Alternatively or additionally to any of the embodiments above, further comprising a trapper balloon disposed within the guidewire lumen and wherein the shaft defines a third lumen in fluid communication with the trapper balloon.

Alternatively or additionally to any of the embodiments above, the shaft defines a fourth lumen and wherein a shapeable member is disposed within the fourth lumen.

Alternatively or additionally to any of the embodiments above, further comprising a compliant balloon coupled to the distal end region of the shaft and wherein the shaft defines a fifth lumen in fluid communication with the compliant balloon.

A method for medical treatment is disclosed. The method comprises: advancing a medical device into body lumen, wherein the medical device comprises: an elongate shaft having a proximal end region and a distal end region, a first lumen defined in the shaft, a second lumen defined in the shaft, wherein the distal end region includes a common lumen region in fluid communication with the first lumen and the second lumen, and a deflectable member disposed within the shaft; wherein a needle is disposed in the second lumen, passes through the common lumen region, and extends distally beyond a distal end of the shaft; proximally retracting the needle into the second lumen; wherein proximally retracting the needle shifts the deflectable member from an open configuration to a closed configuration; and extending a guidewire between the first lumen and the common lumen region.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
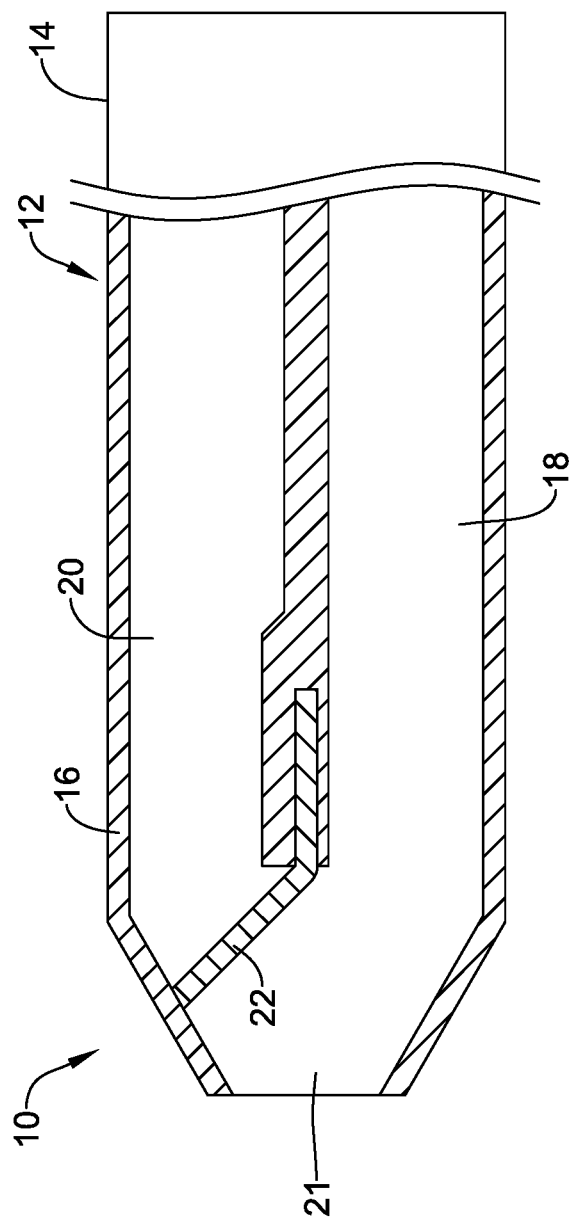
FIG. 1 is a partial cross-sectional side view of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical devices may be used in various medical interventions. Some of these interventions may include providing access to the vascular system, providing access to various chambers of the heart, septal crossings, and the like. Typical, such interventions may involve a number of steps such wire/needle exchanges. Disclosed herein are medical devices that may be used for number of different interventions, may help reduce or simplify an intervention (e.g., by reducing or eliminating steps such as wire/needle exchanges), and the like as well as methods for using such devices.

FIG. 1 is a partial cross-sectional view that schematically depicts an example medical device 10. In this example, the medical device 10 may be considered to be a catheter or dilator. The medical device 10 may include an elongate shaft 12 having a proximal end region 14 and a distal end region 16. One or more lumens may be defined in the shaft 12. For example, the shaft 12 may define a first lumen 18 and a second lumen 20. A common lumen region 21 may be defined in the shaft 12 where the first lumen 18 and the second lumen 20 merge. The common lumen 21 may be in fluid communication with both the first lumen 18 and the second lumen 20.

Figure 2:
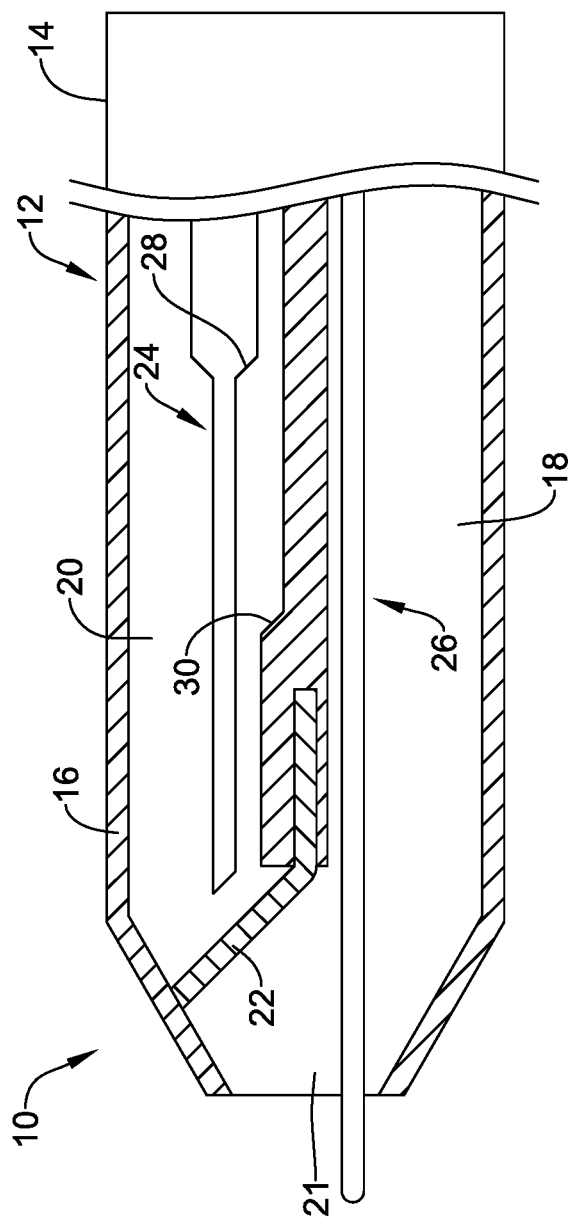
FIG. 2 is a partial cross-sectional side view of an example medical device.

A deflectable member 22 may be disposed within the shaft 12. The deflectable member 22 may be coupled to the shaft 12 in a number of different ways. For example, the deflectable member 22 may extend along a portion of the first lumen 18, may extend along a portion of the second lumen 20, may be attached to an internal region of the shaft 12, may be embedded in a portion of the shaft 12, or the like. In general, the deflectable member 22 may be designed to direct a device passing through the elongate shaft 12 into one of the first lumen 18 and/or the second lumen 20. For example, FIGS. 2-3 illustrate the function of the deflectable member 22. For example, a first medical device 26 may be disposed in the first lumen 18. In some instances, the first medical device 26 may take the form of a guidewire. A second medical device 24 may be disposed in the second lumen 20. In some instances, the second medical device 24 may take the form of a needle or trocar.

Figure 3A:
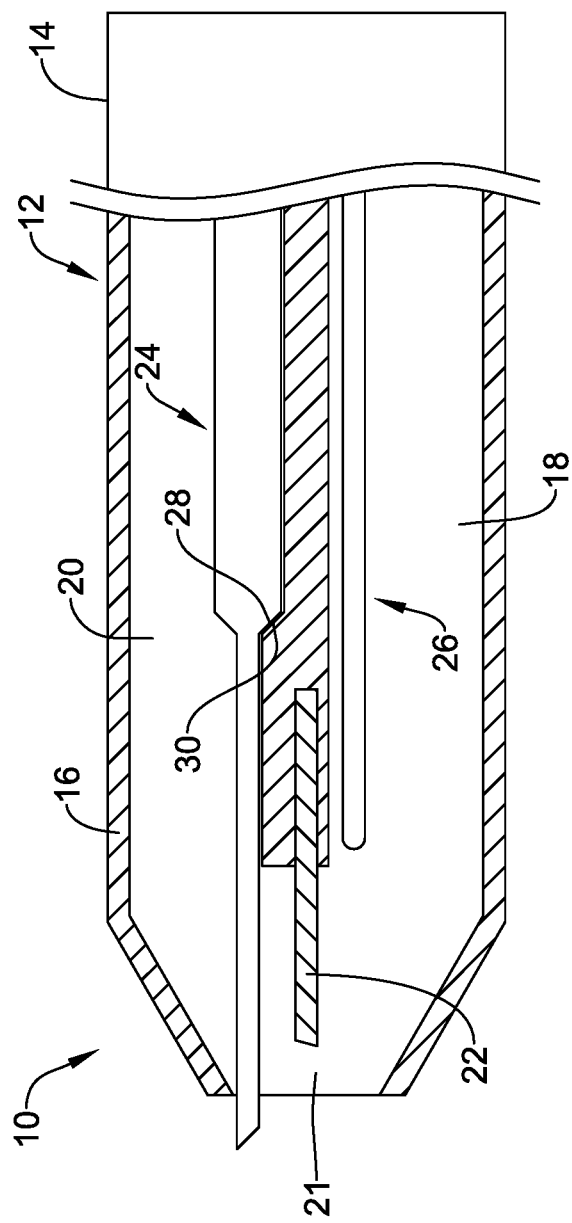
FIG. 3A is a partial cross-sectional side view of an example medical device.
Figure 3B:
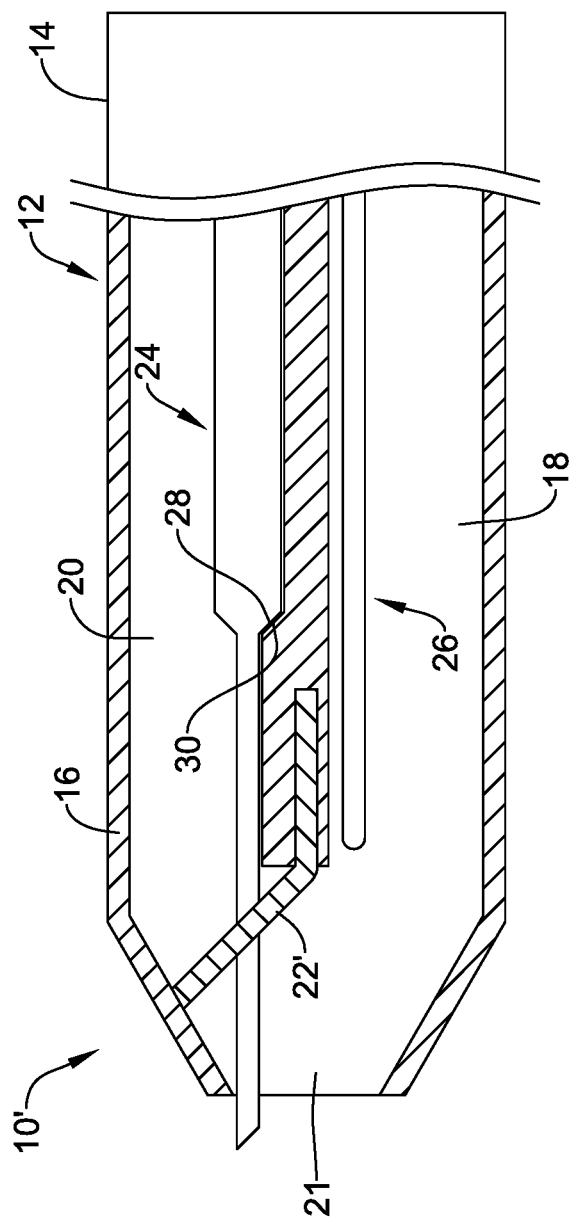
FIG. 3B is a partial cross-sectional side view of an example medical device.

The deflectable member 22 may be designed to shift between a first configuration (e.g., as shown in FIG. 2) and a second configuration (e.g., as shown in FIG. 3A). When the deflectable member 22 is in the first configuration, at least a portion of the deflectable member 22 may obstruct, block, or cover at least a portion of the second lumen 20. This may be desirable for a number of reasons. For example, the deflectable member 22 may help to direct a device (e.g., such as the guidewire 26) to enter into the desired lumen (e.g., the first lumen 18) when the guidewire 26 is backloaded into the shaft 12. For example, when the deflectable member 22 is in the first configuration, the deflectable member 22 may direct the guidewire 26 (e.g., which may be disposed within the common lumen region 21) into the first lumen 18. When the deflectable member 22 is in the second configuration, the deflectable member 22 may allow the needle 24 to move between the common lumen region 21 and the second lumen 20. In addition, the deflectable member 22 may also limit distal migration of the needle 24 within the second lumen 20, which may help to contain the relatively sharp point of the needle 24 within the shaft 12. Other desirable benefits are contemplated.

While the deflectable member 22 may be capable of shifting between configurations, in at least some instance the deflectable member 22 is biased to be in the first configuration. For the purposes of this disclosure, being "biased" may be understood to mean that the deflectable member 22 in its native state or in a state when not subjected to forces that would be capable of shifting the deflectable member 22, the deflectable member 22 is in the first configuration. In order to have this bias, the deflectable member 22 may be elastically deformable/deflectable between the first configuration and the second configuration. This may include forming at least a portion of the deflectable member 22 out of an elastic material, a super-elastic and/or shape memory material, combinations thereof, or the like.

The deflectable member 22 may shift to the second configuration when subject to a force. For example, the needle 24 may be advanced distally into contact with the deflectable member 22 and cause the deflectable member 22 to move or "open" the second lumen 20 (e.g., as shown in FIG. 3A). When the needle 24 is proximally retracted, the deflectable member 22 may shift back to the first configuration (e.g., as shown in FIG. 2).

In other instances, rather than the deflectable member 22 being deflectable, the deflectable member 22 may be replaced by a septum member 22' that makes up part of a medical device 10' similar to other devices disclosed herein. The septum member 22' may extend across the second lumen 20 and be secured to the wall of the shaft 12. Advancing the needle 24 may include advancing the needle 24 through the septum member 22'.

In some instances, the shaft 12 may include additional features. For example, an interior portion of the shaft 12 (e.g., a wall surface along the first lumen 18, the second lumen 20, or both) may have a ridge or ledge 30 that can engage a flange region 28 on the needle 24. This may limit how far the needle 24 can distally migrate within the shaft 12. Because of the shape difference in the wall along one or both of the lumen 18, 20, the first lumen 18, the second lumen 20, or both may have a variable diameter. In some instances, the first lumen 18, the second lumen 20, or both have a substantially constant diameter.

In use, the medical device 10 may be used to provide access to a vascular region. For example, the first lumen 18 may contain the guidewire 26 and the second lumen 20 may contain the needle 24. The needle 24 may be advanced distally to shift the deflectable member 22 to the second configuration (e.g., as shown in FIG. 3A). When doing so, the distal end of the needle 24 may extend out from the end of the shaft 12. When so arranged, the needle 24 can be used to puncture the skin of a patient and gain access to a vascular region. The medical device 10 (which may function as a dilator) can also be advanced into the vascular region. When the medical device 10 is positioned in the vascular region in the desired manner, the needle 24 can be proximally retracted into the second lumen 20, thereby allowing the deflectable member 22 to shift to the first configuration (e.g., as shown in FIG. 2). When so arranged, the guidewire 26 can be advanced out from the shaft 12, into the vascular region, and along the vascular region to a target site.

In other used, the medical device 10 (either loaded with the needle 24 or not loaded with the needle 24) can be backloaded with the guidewire 26. In other words, the proximal end of the guidewire 26 can be pushed through the distal end of the shaft 12 and into the first lumen 18. The deflectable member 22 may help to guide or steer the guidewire 26 into the first lumen 18. This use may allow the medical device 10 to be loaded with the guidewire 26 either for packaging or as part of preparing the medical device for an intervention.

Figure 4A:
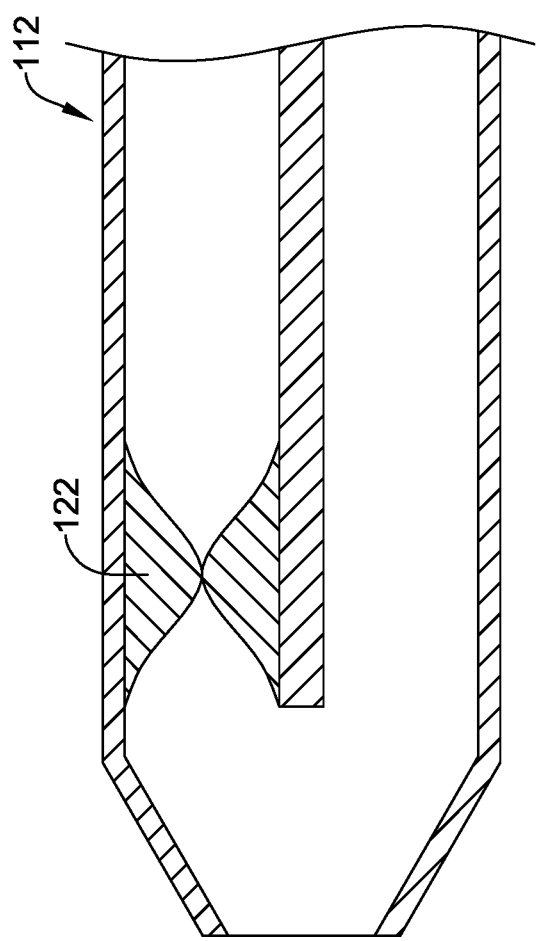
FIGS. 4A-4B are partially cut away side view of a portion of an example medical device.
Figure 4B:
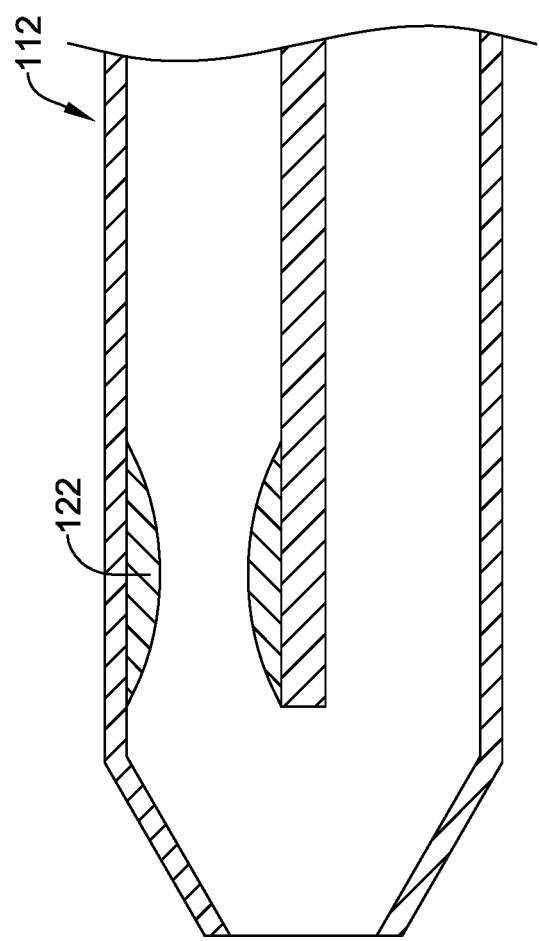

The form, arrangement, and design of the deflectable member 22 may vary. FIGS. 4A-4B to FIGS. 9A-9B illustrate some of the alternative deflectable members contemplated. For example, FIG. 4A illustrates an example deflectable member 122 disposed within a shaft 112. In this example, the deflectable member 122 may take the form of a valve or a "squish valve". The deflectable member 122 may be designed to shift between a first configuration (e.g., as shown in FIG. 4A) and a second configuration (e.g., as shown in FIG. 4B). For example, the deflectable member 122 may be designed to be in the first configuration in a native state and when subjected to forces, the deflectable member 122 may be deform into a flattened second configuration.

Figure 5A:
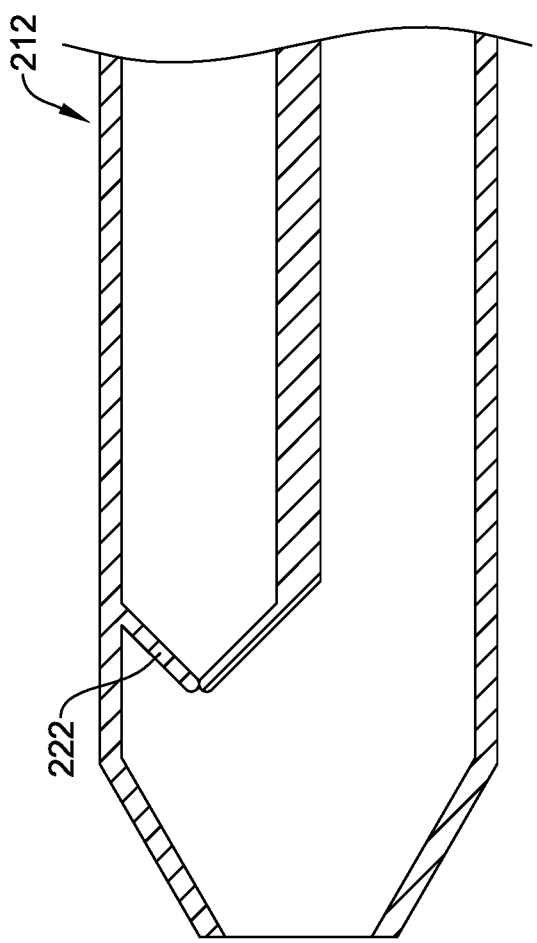
FIGS. 5A-5B are partially cut away side view of a portion of an example medical device.
Figure 5B:
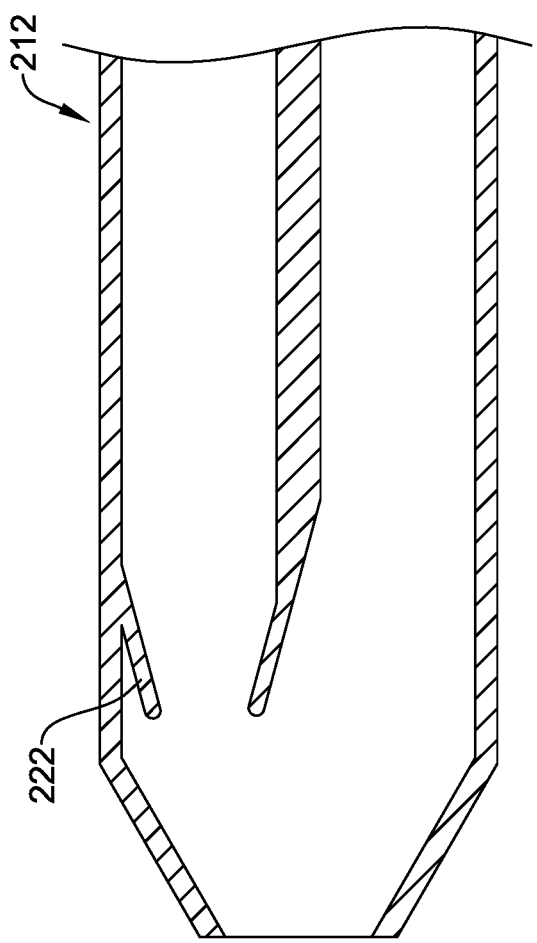
Figure 6A:
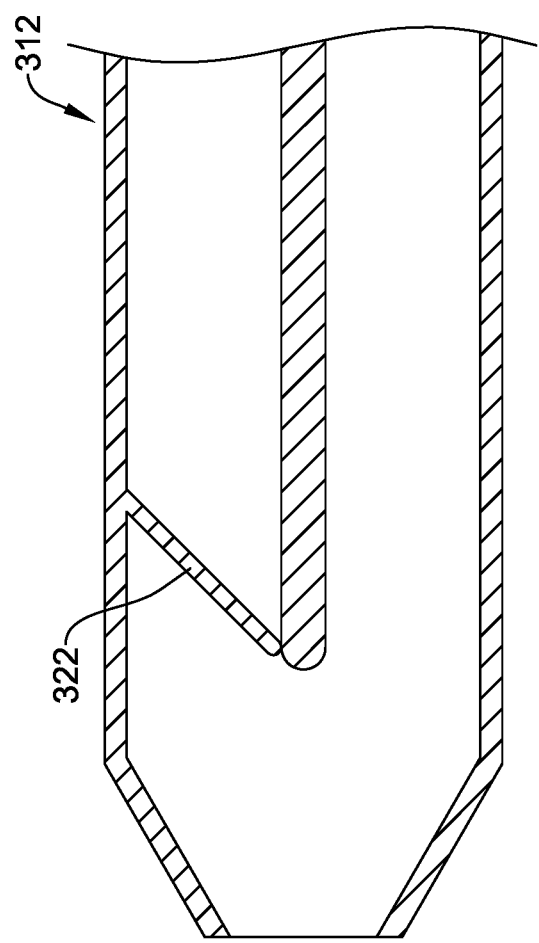
FIGS. 6A-6B are partially cut away side view of a portion of an example medical device.
Figure 6B:
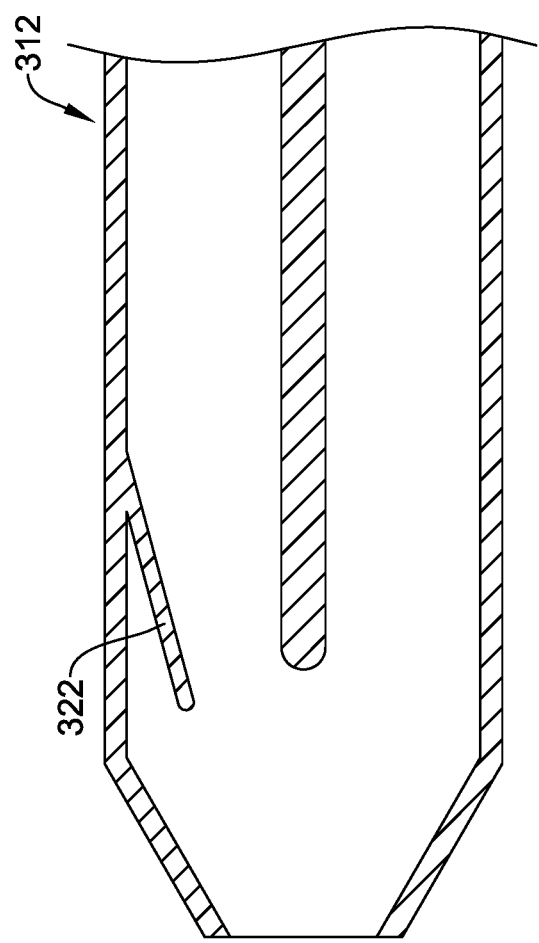
Figure 7A:
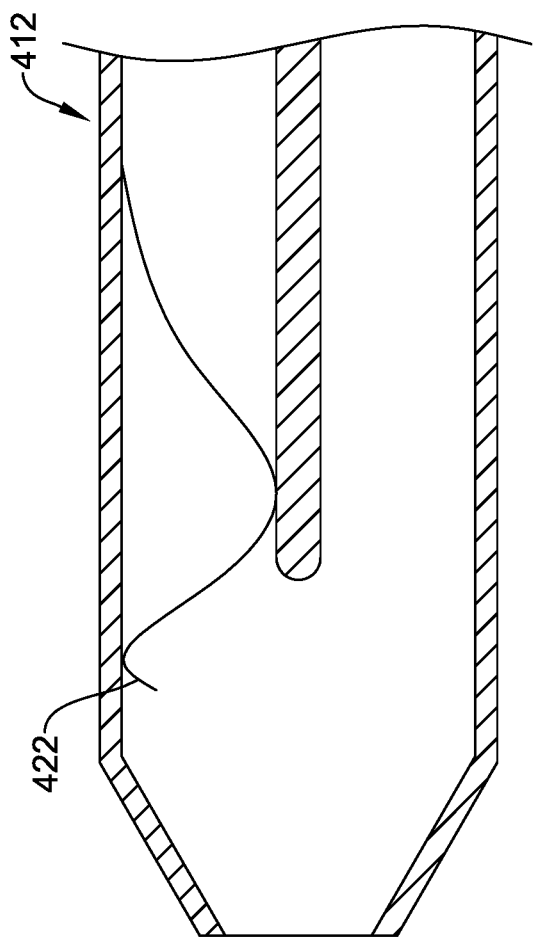
FIGS. 7A-7B are partially cut away side view of a portion of an example medical device.
Figure 7B:
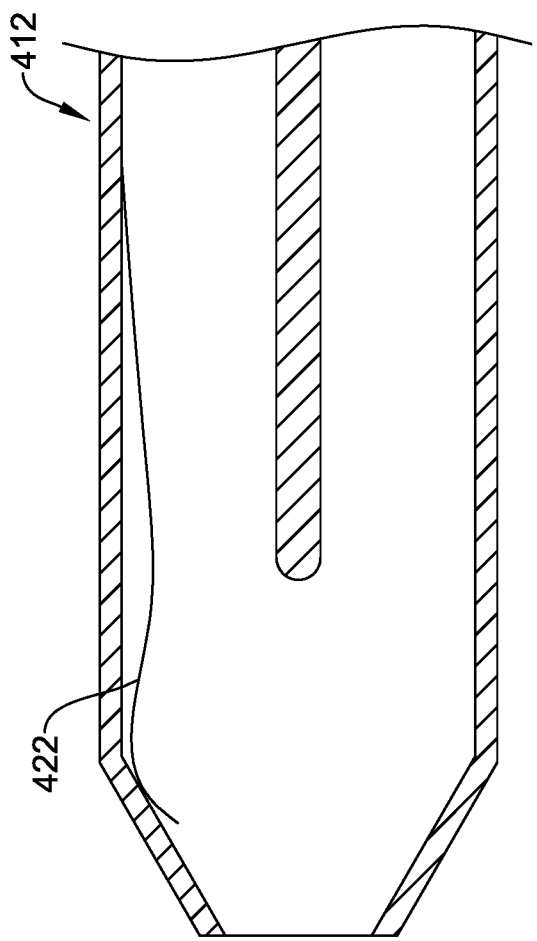
Figure 8A:
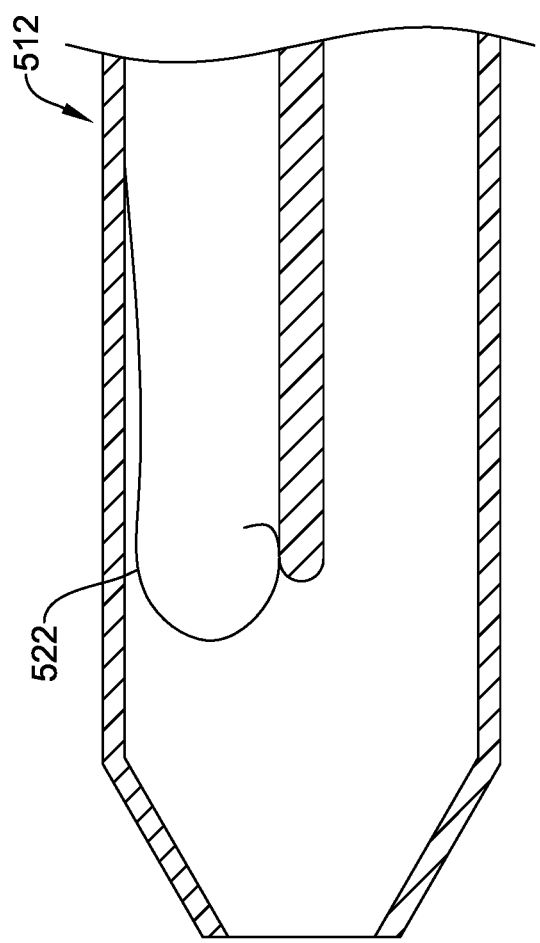
FIGS. 8A-8B are partially cut away side view of a portion of an example medical device.
Figure 8B:
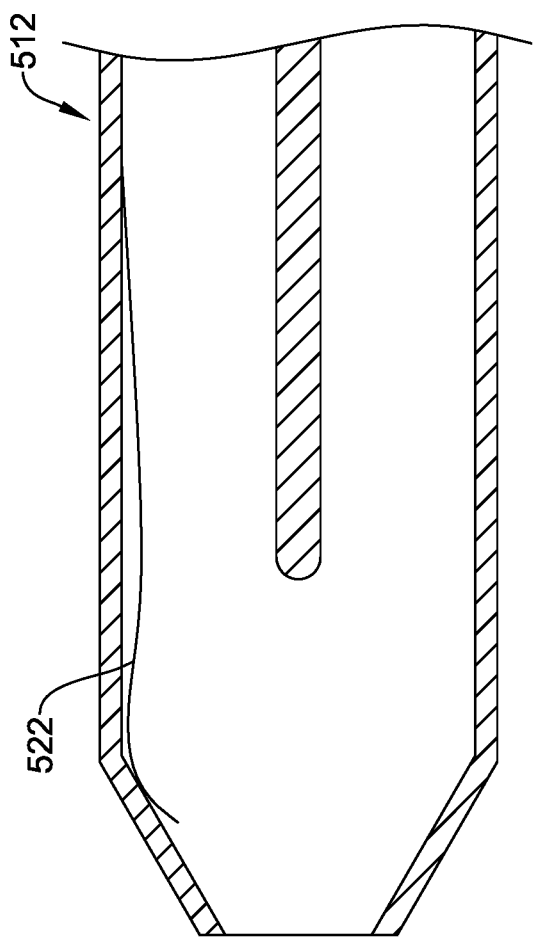
Figure 9A:
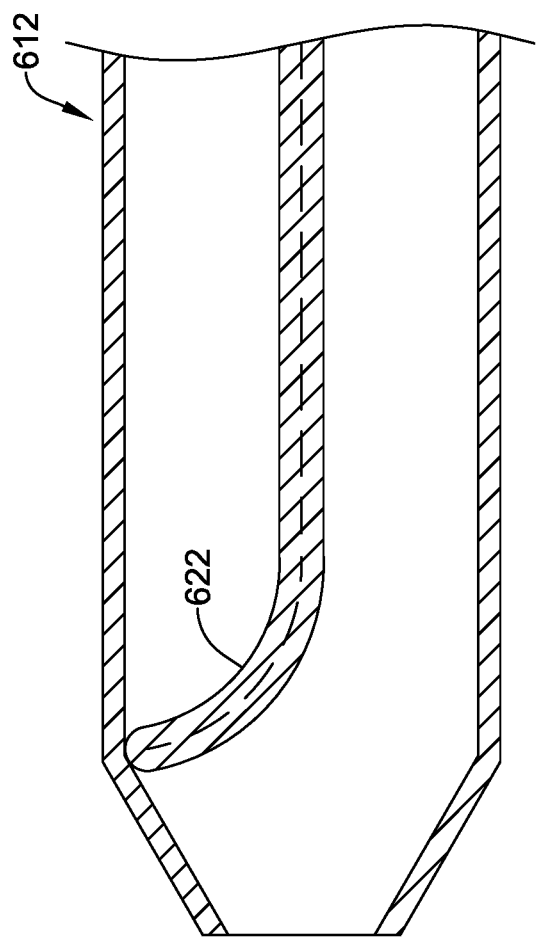
FIGS. 9A-9B are partially cut away side view of a portion of an example medical device.
Figure 9B:
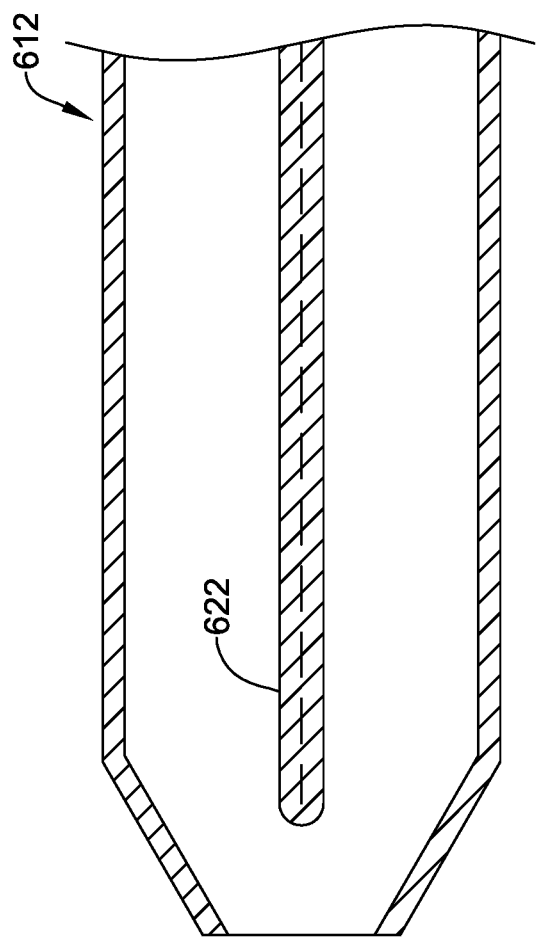

FIG. 5A illustrates an example deflectable member 222 disposed within a shaft 212. In this example, the deflectable member 222 may take the form of a one-way valve. The deflectable member 222 may be designed to shift between a first configuration (e.g., as shown in FIG. 5A) and a second configuration (e.g., as shown in FIG. 5B). FIG. 6A illustrates an example deflectable member 322 disposed within a shaft 312. In this example, the deflectable member 322 may take the form of a deflectable valve or arm. The deflectable member 322 may be designed to shift between a first configuration (e.g., as shown in FIG. 6A) and a second configuration (e.g., as shown in FIG. 6B). FIG. 7A illustrates an example deflectable member 422 disposed within a shaft 412. In this example, the deflectable member 422 may take the form of a collapsible spring wire. The deflectable member 422 may be designed to shift between a first configuration (e.g., as shown in FIG. 7A) and a second configuration (e.g., as shown in FIG. 7B). FIG. 8A illustrates an example deflectable member 522 disposed within a shaft 512. In this example, the deflectable member 522 may take the form of a coil spring or coil spring wire. The deflectable member 522 may be designed to shift between a first configuration (e.g., as shown in FIG. 8A) and a second configuration (e.g., as shown in FIG. 8B). FIG. 9A illustrates an example deflectable member 622 disposed within a shaft 612. In this example, an interior portion of the shaft 612 may make up or define the deflectable member 622. The deflectable member 622 may be designed to shift between a first configuration (e.g., as shown in FIG. 9A) and a second configuration (e.g., as shown in FIG. 9B).

Figure 10:
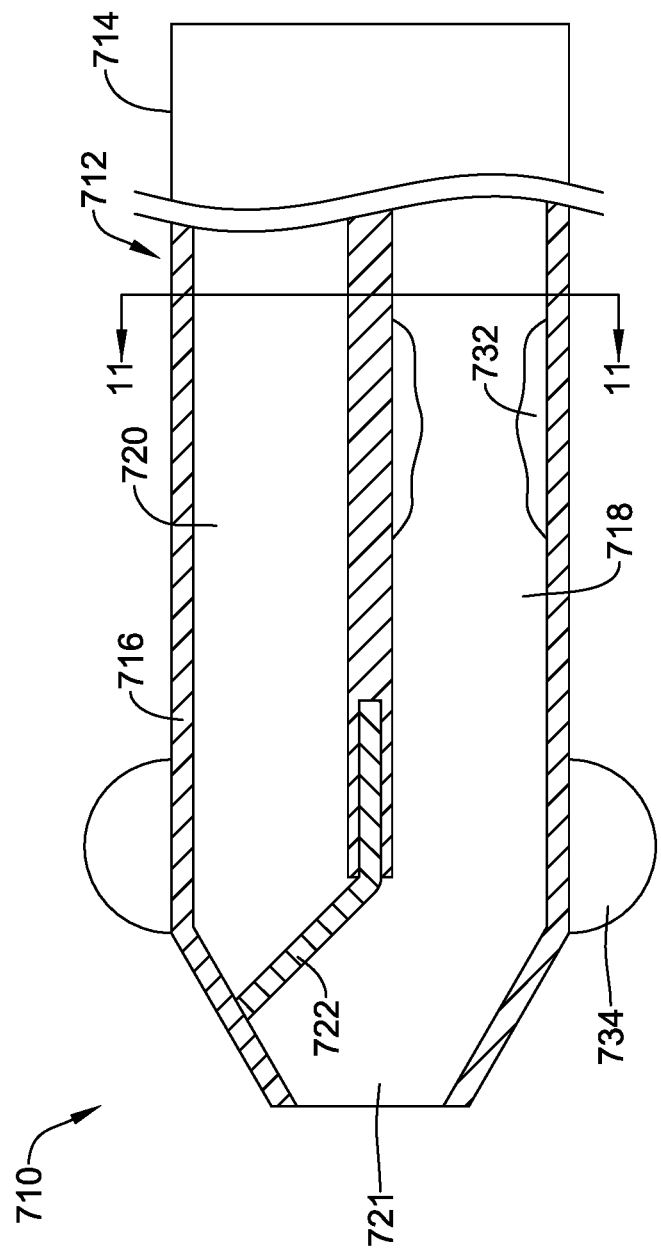
FIG. 10 is a partial cross-sectional side view of an example medical device.

FIG. 10 illustrates another example medical device 710 that may be similar in form and function to other medical devices disclosed herein. The medical device 710 may include an elongate shaft 712 having a proximal end region 714 and a distal end region 716. One or more lumens may be defined in the shaft 712. For example, the shaft 712 may define a first lumen 718 and a second lumen 720. A common lumen region 721 may be defined in the shaft 712 where the first lumen 718 and the second lumen 720 merge. A deflectable member 722 may be disposed within the shaft 712.

The medical device 710 may include an expandable member or trapper balloon 732. The trapper balloon 732 may be disposed within the first lumen 718, within the second lumen 720, may span both lumens (718, 720), or both lumens (718, 720) may include a separate trapper balloon 732. The trapper balloon 732 may be designed to be expanded or otherwise inflated in order to secure a device within a lumen of the shaft 712. For example, the trapper balloon 732 may be inflated in order to secure a guidewire (e.g., the guidewire 26) within the first lumen 718. Other arrangements are contemplated. It should be understood that the trapper balloon 732 may be used with any of the devices disclosed herein, in combination with any of the deflectable members disclosed herein, and in any of the lumens of the shafts disclosed herein, as appropriate.

A distal expandable anchor or balloon 734 may be coupled to the distal end region 716 of the shaft 712. In at least some instance, the distal balloon 734 may be a compliant balloon that is formed from a relatively soft material such as a silicone material. Other materials are contemplated. The shape of the distal balloon 734 may also vary. For example, in some instance, the distal balloon 734 may be designed to expand to a shape that is substantially spherical. In other instances, the balloon 734 may be designed to expand to a shape that may be described as "dumbbell" or "dog bone" shaped. Other shapes are contemplated. It should be understood that the distal balloon 734 may be used with any of the devices disclosed herein, in combination with any of the deflectable members disclosed herein, and in any of the lumens of the shafts disclosed herein, as appropriate.

The distal balloon 734 may provide a number of desirable features. For example, distal balloon 734 may help the medical device 710 navigate or cross portions of the anatomy. For example, the medical device 710 may be used to cross interatrial septum (e.g., at or near the fossa ovalis) and into the left atrium (e.g., in an intervention where access to the left atrium, left atrial appendage, or the like is desired). When doing so, inflating or partially inflating the distal balloon 734 while crossing the septum may help to urge or pull the medical device 710 through septum. Furthermore, after crossing the septum, the distal balloon 734 (e.g., when inflated) may function as an anchor that helps secure the position of the medical device 710 within the left atrium.

Figure 11:
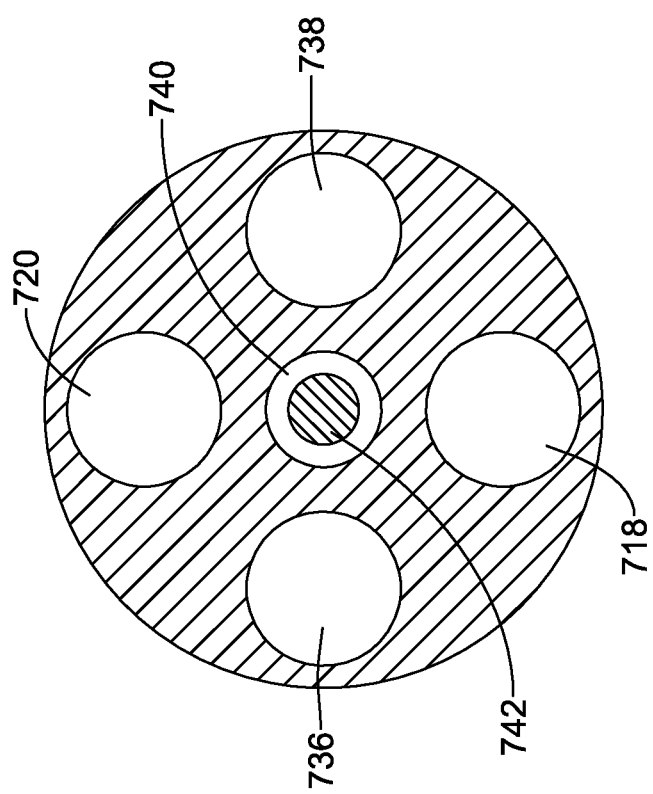
FIG. 11 is a cross-sectional view taken through line 11-11 in FIG. 10.
Figure 12:
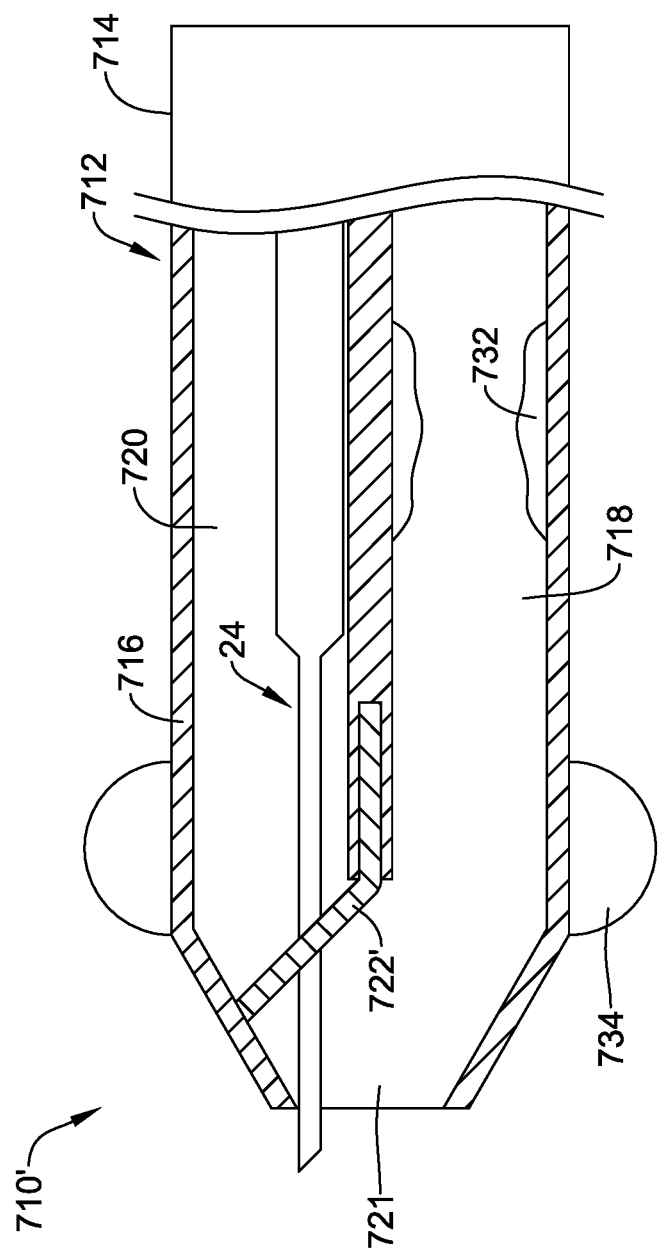
FIG. 12 is a partial cross-sectional side view of an example medical device.

FIG. 11 is a cross-sectional view of the shaft 712 about line 11-11 in FIG. 10. Here it can be seen that a third lumen 736 and/or a fourth lumen 738 may be defined in the shaft 712. The third lumen 736 may be in fluid communication with either the trapper balloon 732 or the distal balloon 734. Likewise, the fourth lumen 738 may be in fluid communication with either the trapper balloon 732 or the distal balloon 734. In some instances, the shaft 712 may also include a fifth lumen 740. A shaping member 742 may be disposed within the fifth lumen 740. The shaping member 742 may take the form of an elastically deformable wire or ribbon that is embedded within or otherwise disposed within the fifth lumen 740. The shaping member 742 allows a user to alter the shape of the shaft 712. For example, a user may bend the shaft 712 so that it has a curved distal portion, which may help with navigation and or use of the medical device 710. It should be understood that the shaping member 742 may be used with any of the devices disclosed herein, in combination with any of the deflectable members disclosed herein, and in any of the lumens of the shafts disclosed herein, as appropriate.

In other instances, rather than the deflectable member 722 being deflectable, the deflectable member 722 may be replaced by a septum member 722' that makes up part of a medical device 710' similar to other devices disclosed herein. The septum member 722' may extend across the second lumen 20 and be secured to the wall of the shaft 12. Advancing the needle 24 may include advancing the needle 24 through the septum member 722'.

The materials that can be used for the various components of the medical device 10 (and/or other medical devices disclosed herein) and the various components thereof may include those commonly associated with medical devices. For simplicity purposes, the following discussion makes reference to the shaft 12 of the medical device 10. However, this is not intended to limit the devices and methods described herein, as the discussion may be applied to other catheter shaft and/or components of any of the medical devices disclosed herein.

The shaft 12 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickeliron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the shaft 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the shaft 12 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the shaft 12 to achieve the same result.

In some embodiments, a degree of Magnetic Resonance Imaging (MRI) compatibility is imparted into the shaft 12. For example, the shaft 12, or portions thereof, may be made of a material that does not substantially distort the image and create substantial artifacts (e.g., gaps in the image). Certain ferromagnetic materials, for example, may not be suitable because they may create artifacts in an MRI image. The shaft 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical device, comprising:
   an elongate shaft having a proximal end region and a distal end region;
   a first lumen defined in the shaft;
   a second lumen defined in the shaft;
   wherein the distal end region includes a common lumen region in fluid communication with the first lumen and the second lumen; and
   a deflectable member disposed within the shaft, the deflectable member being designed to shift between a first configuration where the deflectable member directs a first medical device disposed within the common lumen region into the first lumen and a second configuration where the deflectable member allows a second medical device to move between the common lumen region and the second lumen, wherein a portion of the deflectable member is embedded in an internal region of the shaft.

2. The medical device of claim 1, wherein the deflectable member includes a spring ribbon wire.

3. The medical device of claim 1, wherein the deflectable member includes a one-way valve.

4. The medical device of claim 1, wherein the first lumen, the second lumen, or both have a constant diameter.

5. The medical device of claim 1, wherein along at least a portion of the shaft, the first lumen, the second lumen, or both have a variable diameter.

6. The medical device of claim 1, wherein the deflectable member is biased to be in the first configuration.

7. The medical device of claim 1, further comprising a trapper balloon disposed within the first lumen.

8. The medical device of claim 7, wherein the shaft defines a third lumen in fluid communication with the trapper balloon.

9. The medical device of claim 1, wherein the shaft defines a shaping member fourth lumen and wherein a shaping member is disposed within the shaping member lumen.

10. The medical device of claim 1, further comprising a distal balloon coupled to the distal end region of the shaft.

11. The medical device of claim 10, wherein the shaft defines a distal balloon fifth lumen in fluid communication with the distal balloon.

12. The medical device of claim 10, wherein the distal balloon includes a compliant material.

13. A dilator, comprising:
    an elongate shaft having a proximal end region and a distal end region;
    a guidewire lumen defined in the shaft;
    a needle lumen defined in the shaft;
    wherein the guidewire lumen and the needle lumen merge into a common lumen along the distal end region of the shaft; and
    a deflectable member disposed within the shaft, the deflectable member being designed to shift between a first configuration where the deflectable member is configured to direct a guidewire device from the common lumen into the guidewire lumen and a second configuration where the deflectable member is deflected in order to allow a needle device to move between the common lumen and the needle lumen, wherein the deflectable member includes a spring wire.

14. The dilator of claim 13, wherein the deflectable member is biased to be in the first configuration.

15. The dilator of claim 13, further comprising a trapper balloon disposed within the guidewire lumen and wherein the shaft defines a trapper balloon lumen in fluid communication with the trapper balloon.

16. The dilator of claim 15, wherein the shaft defines a shaping member lumen and wherein a shaping member is disposed within the shaping member lumen.

17. The dilator of claim 16, further comprising a compliant balloon coupled to the distal end region of the shaft and wherein the shaft defines a compliant balloon lumen in fluid communication with the compliant balloon.

18. A method for medical treatment, the method comprising:
    advancing a medical device into a body lumen, wherein the medical device comprises:
    an elongate shaft having a proximal end region and a distal end region,
    a first lumen defined in the shaft,
    a second lumen defined in the shaft,
    wherein the distal end region includes a common lumen region in fluid communication with the first lumen and the second lumen, and
    a deflectable member disposed within the shaft;

wherein a needle is disposed in the second lumen, passes through the common lumen region, and extends distally beyond a distal end of the shaft;

proximally retracting the needle into the second lumen;

wherein proximally retracting the needle shifts the deflectable member from an open configuration to a closed configuration; and extending a guidewire between the first lumen and the common lumen region.

* * * * *